US008073211B2

(12) United States Patent
Halmann

(10) Patent No.: US 8,073,211 B2
(45) Date of Patent: Dec. 6, 2011

(54) METHOD AND APPARATUS FOR GENERATING VARIABLE RESOLUTION MEDICAL IMAGES

(75) Inventor: Nahi Halmann, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 962 days.

(21) Appl. No.: 11/710,696

(22) Filed: Feb. 23, 2007

(65) Prior Publication Data

US 2008/0205715 A1 Aug. 28, 2008

(51) Int. Cl.
*G06K 9/00* (2006.01)
*A61B 8/00* (2006.01)
(52) U.S. Cl. ......................................... 382/128; 600/446
(58) Field of Classification Search .................... 382/128
See application file for complete search history.

(56) References Cited

U.S. PATENT DOCUMENTS

| | | | | |
|---|---|---|---|---|
| 5,471,989 | A | | 12/1995 | Roundhill et al. |
| 6,106,472 | A | * | 8/2000 | Chiang et al. ................. 600/447 |
| 6,278,975 | B1 | * | 8/2001 | Brant et al. .................... 704/275 |
| 6,440,072 | B1 | * | 8/2002 | Schuman et al. ............. 600/437 |
| 6,549,214 | B1 | * | 4/2003 | Patel et al. .................... 345/660 |
| 6,569,097 | B1 | * | 5/2003 | McMorrow et al. .......... 600/437 |
| 6,980,419 | B2 | * | 12/2005 | Smith et al. ............... 361/679.41 |
| 2001/0041991 | A1 | * | 11/2001 | Segal et al. ........................ 705/3 |
| 2003/0073894 | A1 | * | 4/2003 | Chiang et al. ................. 600/407 |
| 2005/0154303 | A1 | * | 7/2005 | Walker et al. ................. 600/443 |
| 2005/0228281 | A1 | * | 10/2005 | Nefos ........................... 600/446 |
| 2005/0288584 | A1 | * | 12/2005 | McMorrow et al. .......... 600/437 |
| 2006/0025684 | A1 | * | 2/2006 | Quistgaard et al. ........... 600/441 |

OTHER PUBLICATIONS

Chinese Foreign Official Action for Application No. 200810081372. 6, Date of Issue: Dec. 31, 2010, Applicant: General Electric Company, Methods and Apparatus for Variable Resolution Medical Images, GE Reference No. 223677.

* cited by examiner

*Primary Examiner* — David Zarka
(74) *Attorney, Agent, or Firm* — Dean D. Small; The Small Patent Law Group

(57) ABSTRACT

A hand carried medical imaging device includes a probe configured to acquire raw medical image data, an integrated display, a data memory configured to store the acquired raw medical image data, a back end processor, and a user interface operably coupled to the back end processor configured to receive commands from a user and to instruct the back end processor to display the produced medical image on the integrated display at a first resolution, and to either produce and send either the medical image at the second, higher resolution, to send the acquired raw image data, or both, to the external device, in accordance with the commands from the user.

23 Claims, 5 Drawing Sheets

METHOD AND APPARATUS FOR GENERATING VARIABLE RESOLUTION MEDICAL IMAGES

BACKGROUND OF THE INVENTION

This invention relates generally to handheld and hand-carried ultrasound (or other medical imaging) systems having integrated displays.

Handheld and hand-carried ultrasound systems often include an integrated display (usually an LCD) that allows the user to view the images while scanning as well as retrieve images from internal storage device. Often, these systems are used in conjunction with external medical devices such as a PACS (Picture Archiving and Communication System) system, a workstation, and/or an external printer. Often, these external systems can support display resolutions higher than that achievable with the internal display of the hand-carried ultrasound system. However, images from the handheld or hand-carried ultrasound systems do not provide image data at a resolution sufficient to support the higher display resolutions of the external systems.

BRIEF DESCRIPTION OF THE INVENTION

In an exemplary embodiment, a hand carried medical imaging device is provided that includes a probe configured to acquire raw medical image data, an integrated display, a data memory configured to store the acquired raw medical image data, a back end processor, and a user interface operably coupled to the back end processor configured to receive commands from a user and to instruct the back end processor to display the produced medical image on the integrated display at a first resolution. The user interface is also configured to either produce and send either the medical image at a second, higher resolution, to send the acquired raw image data, or both, to the external device, in accordance with the commands from the user.

In another exemplary embodiment, a method for operating a hand carried medical imaging device is provided. The device includes a probe configured to acquire raw medical image data, an integrated display configured to display a medical image, a data memory configured to store the acquired raw medical image data, a back end processor and a user interface. The user interface is operably coupled to the back end processor and is configured to receive commands from a user and to instruct the back end processor to display a produced medical image on the integrated display at a first resolution. The user interface is also configured to either produce and send either the medical image at a second, higher resolution, to send the acquired raw image data, or both, to an external device, in accordance with the commands from the user. The method includes storing raw medical image data in a coordinate system of the probe, and, in accordance with instructions received via the user interface, either performing a scan conversion on the raw medical image data and displaying a resulting medical image at a first resolution on the integrated display; or at least one of transferring raw data to the external device for further processing or storage, or performing a scan conversion on the raw medical image data and displaying a resulting medical image at a second, higher resolution on an external display.

In yet another exemplary embodiment, a machine readable medium or media is provided having recorded thereon instructions configured to instruct a processor in a hand carried medical imaging device to acquire and store raw medical image data in a coordinate system of a probe on a data memory, and, in accordance with instructions received via a user interface, either perform a scan conversion on the raw medical image data and display a resulting medical image at a first resolution on an integrated display; or at least one of transfer raw data to an external device for further processing or storage, or perform a scan conversion on the raw medical image data and display a resulting medical image at a second, higher resolution on an external display.

Figure 1:
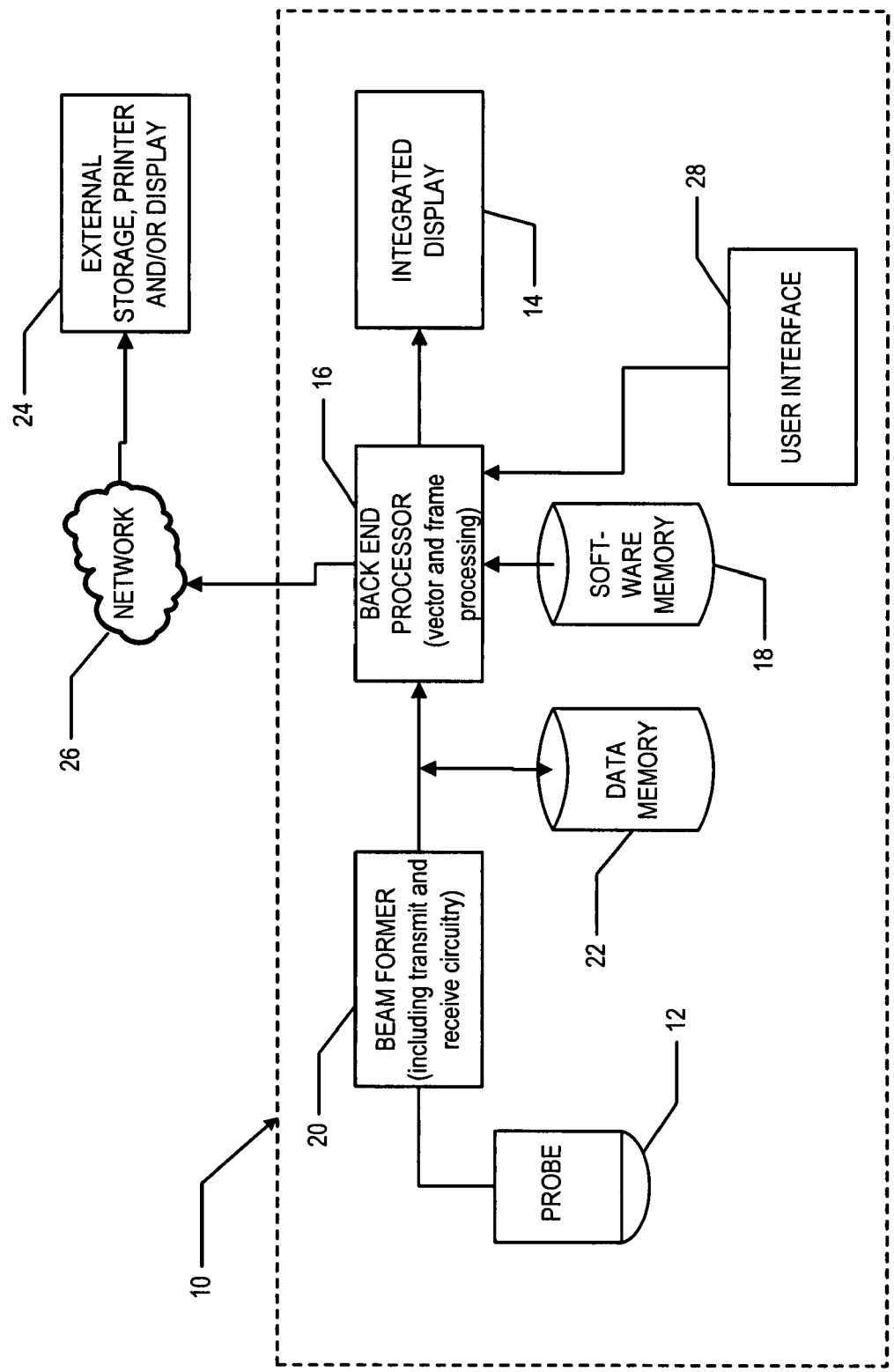
FIG. 1 is a block diagram of a hand carried or hand-held medical imaging device having a probe or transducer configured to acquire raw medical image data formed in accordance with various embodiments of the invention.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

DETAILED DESCRIPTION OF THE INVENTION

As used herein, an element or step recited in the singular and proceeded with the word "a" or "an" should be understood as not excluding plural said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Technical results of the present invention include the transmission of high resolution medical images and/or high resolution raw medical image data across a wired or wireless network, or across a dedicated connection. The present description details how these results are achieved in some embodiments of the present invention.

FIG. 1 is a block diagram of a handheld or hand carried medical imaging device 10 having a probe or transducer 12 configured to acquire raw medical image data. In some embodiments, probe 12 is an ultrasound transducer and hand carried medical imaging device 10 is an ultrasound imaging apparatus. An integrated display 14 (e.g., an internal display) is also provided and is configured to display a medical image. A data memory 22 stores acquired raw image data, which may be processed by a beam former 20 in some embodiments of the present invention.

To display a medical image using probe 12, a back end processor 16 is provided with a software or firmware memory 18 containing instructions to perform frame processing, scan conversion, and resolution selection using acquired raw medical image data from probe 12, possibly further processed by beam former 20 in some configurations. Dedicated hardware may be used instead of software for performing scan conversion, or a combination of dedicated hardware and software, or software in combination with a general purpose processor or a digital signal processor. Once the requirements for such software and/or hardware and/or dedicated hardware are gained from an understanding of the descriptions of embodiments of the invention contained herein, the choice of any particular implementation may be left to a hardware engineer and/or software engineer. However, for purposes of the present disclosure, any dedicated and/or special purpose hardware or special purpose processor is considered subsumed in the block labeled "back end processor 16."

Software or firmware memory 18 can comprise a read only memory (ROM), random access memory (RAM), a miniature hard drive, a flash memory card, or any kind of device (or devices) configured to read instructions from a machine-readable medium or media. The instructions contained in software or firmware memory 18 further include instructions to produce a medical image of suitable resolution for display on integrated display 14, and to send acquired raw image data stored in a data memory 22 to an external device 24 in a higher resolution, for example, a resolution higher than the highest resolution that can be displayed on integrated display 14. The image data of higher resolution and/or the raw medical image data itself may be sent from back end processor 16 to external device 24 via a wired or wireless network (or direct connection, for example, via a serial or parallel cable or USB port) 26 under control of processor 16 and user interface 28. In some embodiments, external device 24 may be a computer or a workstation having a display. In some other embodiments, external device 24 may be a separate external display or a printer capable of receiving image data from hand carried medical imaging device 10 and of displaying or printing images having greater resolution than integrated display 14.

A user interface 28 (that may also include integrated display 14) is provided to receive commands from a user and to instruct back end processor 16 to display the acquired raw image data on integrated display 14, send the acquired raw image data to external device 24 in a higher resolution than that displayable on integrated display 14, or both, in accordance with the commands from the user.

Figure 2:
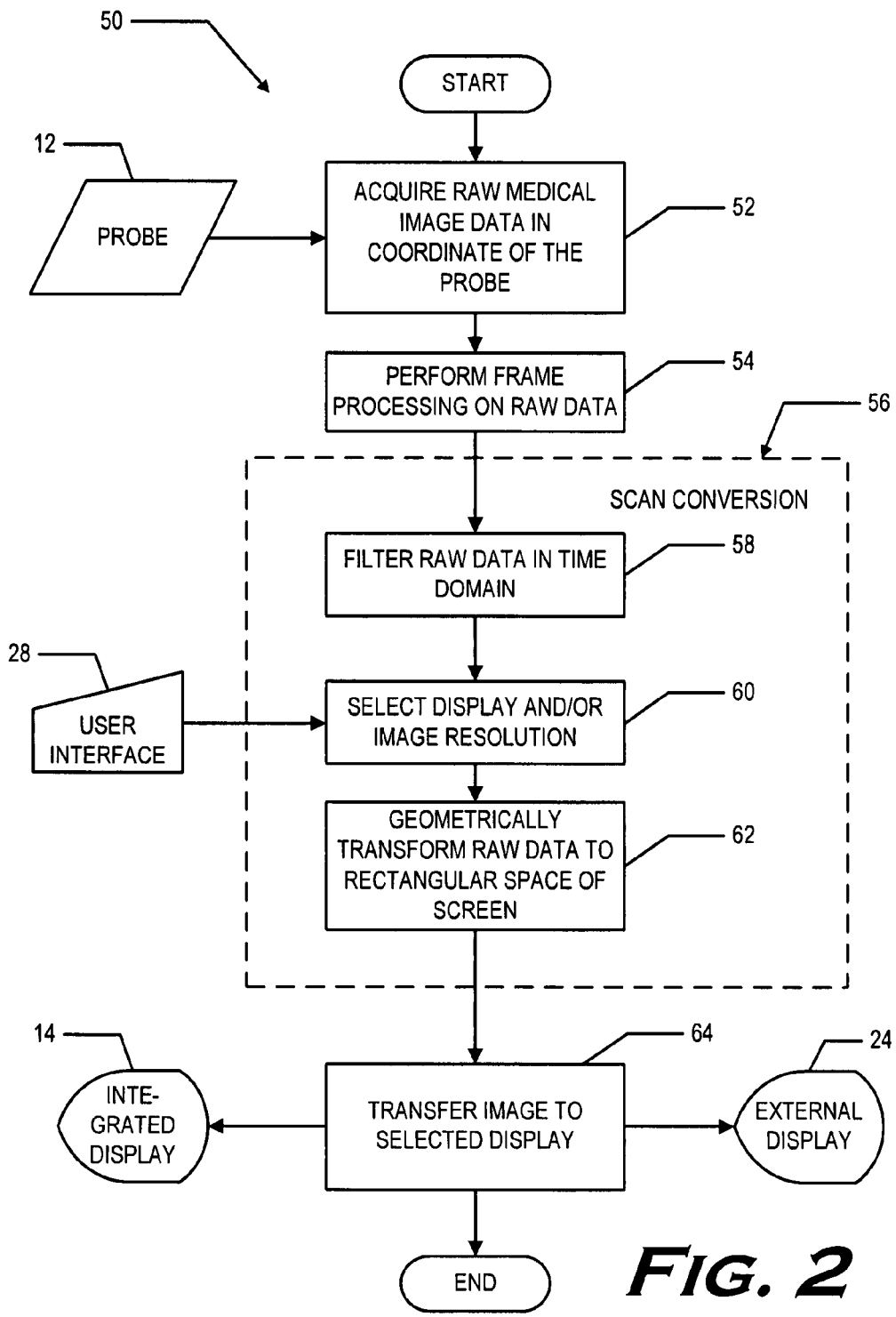
FIG. 2 is a flow chart of a method that can be performed by the hand carried medical imaging device of FIG. 1.

FIG. 2 is a flow chart 50 of a method that can be performed by the hand carried medical imaging device 10 of FIG. 1. Referring to FIG. 2, at 52, hand carried medical imaging device 10 is operated to acquire raw medical image data in the coordinates of medical transducer or probe 12. This step of the method may involve the cooperation of beam former 20, data memory 22 (where the raw medical image data is stored), and back end processor 16, under the instruction of software stored in software memory 18. At 54, frame processing is performed on raw medical image data by back end processor 16 under instruction of software stored in software memory 18. In some embodiments of the present invention, this step of the method includes accessing stored raw medical image data from data memory 22.

At 56, a scan conversion process is carried out that produces geometrically transformed data with a resolution appropriate for the size of display on which the medical image data is to be displayed as an image. More particularly, raw data is filtered in the time domain at 58. The temporal filtering at 58 can include, for example, frame averaging, so that each image frame that is displayed comprises data from more than one data frame. Temporal filtering also allows the separation of the display frame rate from the input raw data rate. More particularly, the rate at which a piezoelectric front end (e.g., a piezoelectric element 12 in an ultrasound imaging apparatus 10) scans and/or obtains data for image frames can be faster or slower than the display rate of the frames themselves. Next, at 60, a user selects a display and/or image resolution using user interface 28. For example, if integrated display 14 in hand carried medical imaging device 10 has a maximum resolution of 320×320 pixels, the user can select that the image be displayed on this device in up to 320×320 resolution.

If an external display 24 is selected (or an external storage device or printer), the user can specify the resolution of the image to be displayed on external display device 24 (or saved to the external storage device or printed on the printer). Next, at 62, the filtered data from 58 is geometrically transformed to the rectangular space of the display, in accordance with the selected display and/or image resolution from 60. For example, each line of echo raw data may comprise 1000 samples, wherein probe 12 "illuminates" and gathers data from a fan-like region of 100 lines, each with 1000 samples. The conversion at 62 transforms the data from a polar to a Cartesian coordinate system (for example) using averaging over a number of pixels (e.g., bilinear or trilinear) to reduce interpolation. In the case of bilinear averaging, each point on the result of the interpolation is the result of interpolating four neighboring data points. The neighboring points are, for example, four points from two rotated vectors that are averaged, each point being weighted appropriately. Finally, at 64, the geometrically transformed data from 62 is transferred either to integrated display 14 or external display 24, in accordance with the selection made at 60.

As a result, in some embodiments of the present invention, medical images can be displayed in a relatively low resolution (up to the highest resolution available) on relatively small integrated display 14, or displayed (or stored or printed) on an external device 24, possibly at a much higher resolution.

Flow chart 50 of FIG. 2 contemplates an embodiment in which scan conversion 56 for external devices 24 is performed by hand carried medical imaging device 10. However, in some embodiments, scan conversion 56 is not performed by hand carried medical imaging device 10 for external devices 24. Instead, raw medical image data from data memory 22 (optionally processed by beam former 20) is transferred directly from hand carried medical imaging device 10 to external storage, printer, and/or display 24 for further processing, as necessary. Flow chart 68 of FIG. 3 shows an example of one such embodiment.

Figure 3:
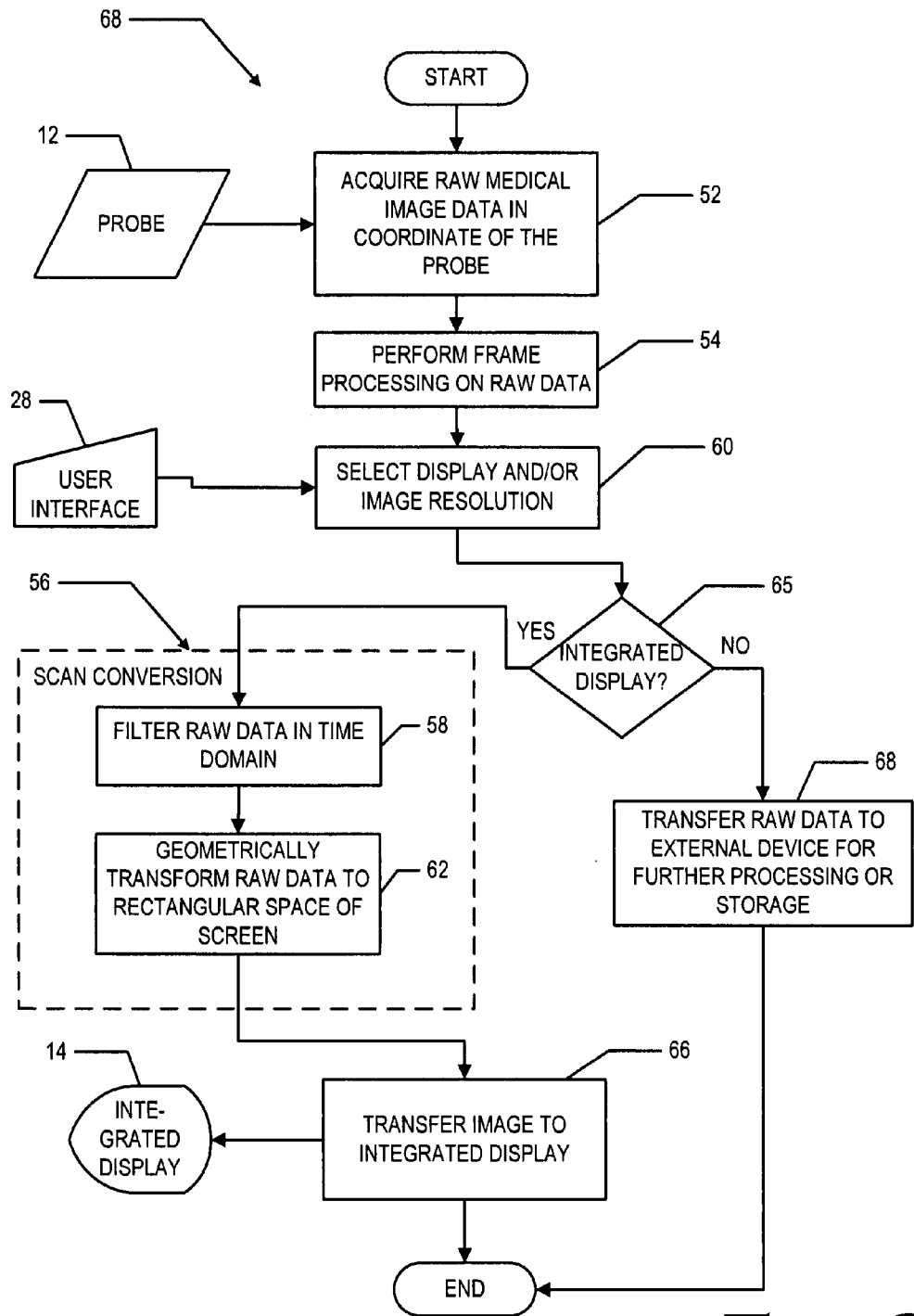
FIG. 3 is a flow chart of another method that can be performed by the hand carried medical imaging device of FIG. 1.

Referring to FIG. 3, at 52, hand carried medical imaging device 10 is operated to acquire raw medical image data in the coordinates of medical transducer or probe 12. This step of the method may involve the cooperation of beam former 20, data memory 22 (where the raw medical image data is stored), and back end processor 16, under the instruction of software stored in software memory 18. At 54, frame processing is performed on raw medical image data by back end processor 16 under instruction of software stored in software memory 18. In some embodiments of the present invention, this step of the method includes accessing stored raw medical image data from data memory 22, and may include either or both reading or storing the raw medical image data. (Thus, whenever "raw medical image data" is referred to herein, it may refer either to raw medical image data, with or without frame processing.) Next, at 60, information is obtained from the user of hand carried medical imaging device 10 concerning whether to display a medical image on integrated display 14, or to send it to an external device 24 for display, storage, and/or further processing.

If the user selected that the data be displayed on integrated display 14, then a decision is made at 65 to subject the raw medical image data to scan conversion at 56. In this case, the raw medical image data is filtered in the time domain at 58 and then geometrically transformed (at the appropriate resolution for integrated display 14 or at a lesser resolution chosen by the user) to the rectangular space of display 14. The image is then transferred to integrated display 14 at 66.

On the other hand, if the user selected that data be sent to external device 24, the raw medical image data itself is sent (in at least one embodiment, without further image processing or scan conversion) to external device 24 for further processing, storage, and/or display.

It should be understood that the functionalities of flow chart 50 and flow chart 68 may be combined in various ways, and that these flow charts are not intended to limit the functionality of various embodiments of the present invention. For example, in some embodiments of the present invention, both high resolution images (as in flow chart 50) and raw medical image data (as in flow chart 68) can be exported to an external device 24, or either, depending upon a selection made by the user and entered into user interface 28. Also, like steps in flow charts 50 and 68 represent similar processes.

Figure 4:
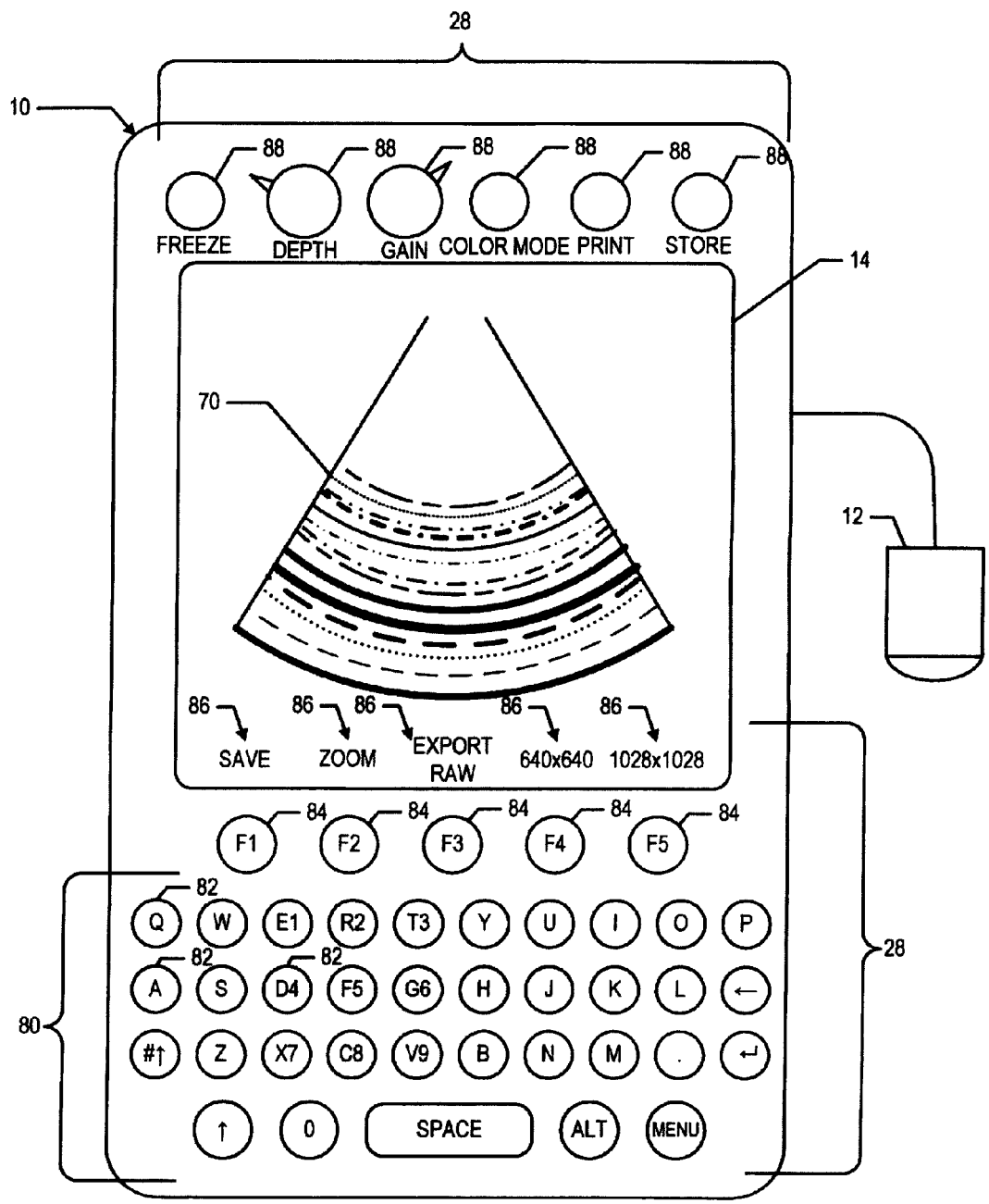
FIG. 4 is a pictorial drawing of a hand carried medical imaging device formed in accordance with an embodiment of the present invention.

FIG. 4 is a pictorial drawing of an embodiment of hand carried medical imaging device 10 of the present invention. Hand carried medical imaging device 10 includes the display 14, for example, a 320×320 pixel color LCD display (on which a medical image 70 may be displayed) and the user interface 28. In some embodiments of the present invention, a typewriter-like keyboard 80 of buttons 82 is included in user interface 28, as well as one or more soft keys 84 that may be assigned functions in accordance with the mode of operation of hand carried medical imaging device 10. A portion of display 14 may be devoted to labels 86 for soft keys 84. For example, the labels shown in FIG. 4 allow a user to save the current raw medical image data, to zoom in on a section of image 70 on display 14, to export raw medical image data to an external device 24, or to display (or export) an image having a resolution of either 640×640 pixels or 1028×1028 pixels on an external device 24 that includes a display. The device may also have additional keys and/or controls 88 for special purpose functions, which may include, but are not limited to "freeze," "depth control," "gain control," "color-mode," "print," and "store."

Figure 5:
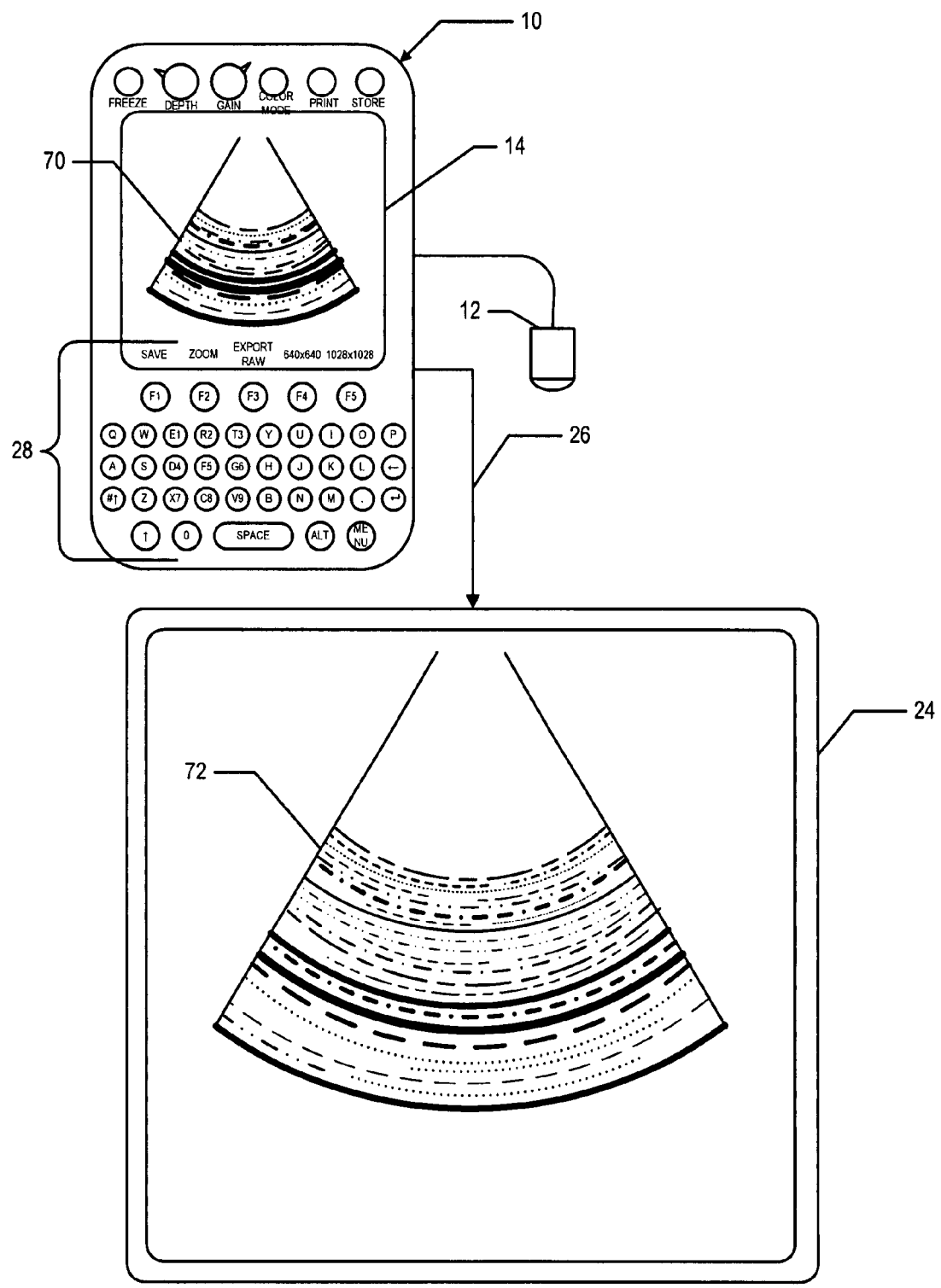
FIG. 5 is a pictorial drawing illustrating a hand carried medical imaging device directly connected to an external device in accordance with various embodiments of the invention.

FIG. 5 is a pictorial schematic drawing of hand carried medical imaging device 10 directly connected to an external device 24. Because hand carried medical imaging device 10 is capable of storing raw medical image data for export to external device 24 and/or processing data at a higher resolution than is available with integrated display 14, external device 24 can display a higher resolution version 72 of image 70. For example, external device 24 can have a display 24 that displays 1024×1024 pixels, whereas integrated display 14 may be capable of displaying only 320×320 pixels on account of its small size.

Thus, some embodiments of the present invention include the capability of visualizing image data in real time on integrated display 14 (albeit at relatively low resolution) while hand carried medical imaging device 10 is used on a patient, with raw medical image data stored in memory 22. Then, if needed, the raw medical image data can be transferred to an external memory, printer, or display 24 where another scan conversion can be performed. Neither the transfer nor the other scan conversion need be performed at the same time as image data is visualized on integrated display 14, nor need either be done at the same site where the image data is acquired. In cases in which scan conversion is done by hand carried medical imaging device 10 for an external device 24, images once displayed at relatively low resolution on integrated display 14 can be selected, and then regenerated and displayed at higher resolution on external device 24. In these cases, less time is required than is required to transfer the raw medical imaging data to external device 24. Also, there is no universal standard for transferring raw medical imaging data, but the high resolution images can be generated in JPEG or DICOM format and sent to an external display device 24. If only selected images are being sent in this manner, transmission between hand carried medical imaging device 10 and external device 24 can be made very efficient.

Other embodiments of the present invention provide a machine readable medium or media 18 having recorded thereon instructions configured to instruct a processor 16 in a hand carried medical imaging device 10 to acquire and store raw medical image data 52 in a coordinate system of probe 12 on a data memory 22, and, in accordance with instructions received via a user interface, either perform a scan conversion 56 on the raw medical image data and display 64 a resulting medical image 70 at a first resolution on an integrated display 14; or at least one of transfer raw data 68 to an external device 24 for further processing or storage, or perform a scan conversion 56 on the raw medical image data and display 64 a resulting medical image 72 at a second, higher resolution on an external display 24.

Embodiments of the present invention are not limited to ultrasound machines as a hand carried medical imaging device 10. For example, images can be provided from other probes 12, such as a medical endoscope probe.

While the invention has been described in terms of various specific embodiments, those skilled in the art will recognize that the invention can be practiced with modification within the spirit and scope of the claims.

What is claimed is:

1. A portable ultrasound system comprising:
   a probe to acquire raw ultrasound data of an object;
   an integrated display to present ultrasound images generated from the raw ultrasound data;
   a memory to store the raw ultrasound data without frame processing as acquired by the probe; and
   a processor configured to process the raw ultrasound data without frame processing as acquired by the probe using a reconstruction process to reconstruct a lower resolution image and a higher resolution image of an imaged body based on the stored raw ultrasound data without frame processing as acquired by the probe, the processor further configured to send the lower resolution image to the integrated display for presentation to a user and the higher resolution image to an external display device for presentation to the user, the processor further configured to send the raw ultrasound data without frame processing as acquired by the probe to an external device for at least one of storage or further processing.

2. The portable ultrasound system of claim 1, further comprising a user interface whereby the processor receives user command to store an image at a user preferred resolution.

3. The portable ultrasound system of claim 1, further comprising a beam former operably coupled to the probe, and wherein the memory is configured to store the acquired raw ultrasound data after the acquired raw ultrasound data has been processed by the beam former.

4. The portable ultrasound system of claim 1, wherein the user interface includes a keyboard of buttons and at least one soft key, and wherein the soft key is labeled on the integrated display.

5. The portable ultrasound system of claim 1, further comprising software memory with instructions configured to control the processor, and wherein the software memory further comprises a plug-in flash memory card.

6. The portable ultrasound system of claim 1, wherein the external device is a printer, and the processor is configured to send a medical image at a second, higher resolution to the printer.

7. The portable ultrasound system of claim 6, wherein the processor is configured to send the medical image at the second, higher resolution, to the printer using one of a wired or wireless medium.

8. The portable ultrasound system of claim 1, wherein the raw ultrasound data without frame processing as acquired by the probe is a probe coordinate system.

9. The portable ultrasound system of claim 1, wherein the external device comprises another portable ultrasound system.

10. The portable ultrasound system of claim 1, wherein the memory is a long term storage memory.

11. The portable ultrasound system of claim 1, wherein the stored raw ultrasound data without frame processing as acquired by the probe is stored to allow one or more images to be reconstructed in a plurality of planes in at least one of real time or at a later time.

12. A method for operating a portable ultrasound system having a probe, the method comprising:
   acquiring raw ultrasound data using the probe;
   presenting an ultrasound image on an integrated display;
   storing raw ultrasound data without frame processing as acquired by the probe in a memory;
   processing the raw ultrasound data without frame processing as acquired by the probe using a reconstruction process to perform image reconstruction at, at least one of multiple scan size or image resolution and;
   producing a medical image of a first, lower resolution, to display on the integrated display, producing and sending a medical image at a second, higher resolution, to an external device or sending the raw ultrasound data without frame processing as acquired by the probe to an external device; and
   receiving a user command via a user interface, whereby a processor performs one of displaying the produced medical image of a first resolution on the integrated display at a first resolution, or to at least one of produce and send the medical image at the second, higher resolution, to an external device or send the raw ultrasound data without frame processing as acquired by the probe to the external device.

13. The method of claim 12, wherein said method comprises, in accordance with instructions received via the user interface, one of:
   performing a reconstruction using the raw ultrasound data without frame processing as acquired by the probe and displaying a resulting medical image, at a first resolution on the integrated display; and
   performing a reconstruction using the raw ultrasound data without frame processing as acquired by the probe and displaying the resulting medical image at the second, higher resolution on the external display or a printer.

14. The method of claim 13, further comprising sending the resulting medical image at the second, higher resolution to the external display or printer via one of a wireless, or a wired medium.

15. The method of claim 12, wherein said method comprises, in accordance with instructions received via the user interface, one of:
   performing a reconstruction using the raw ultrasound data without frame processing as acquired by the probe or
   transferring the raw ultrasound data to the external device for further processing or storage.

16. The method of claim 12, wherein the portable ultrasound system further comprises a beam former operably coupled to the probe, and said method further comprises storing the raw ultrasound data without frame processing as acquired by the probe after the raw ultrasound data without frame processing as acquired by the probe has been processed by the beam former.

17. The method of claim 12, wherein the user interface includes a keyboard of buttons and at least one soft key, and said method further comprises labeling the soft key on the integrated display.

18. The method of claim 12, further comprising storing the raw ultrasound data without frame processing as acquired by the probe in a probe coordinate system.

19. A non-transitory machine readable medium or media having recorded thereon to:
   acquire raw ultrasound data using a probe;
   present an ultrasound image on an integrated display;
   store raw ultrasound data without frame processing as acquired by the probe in a probe coordinate system on a memory;
   process the stored raw ultrasound data without frame processing as acquired by the probe to perform a reconstruction process using the raw ultrasound data without frame processing as acquired by the probe to reconstruct a lower resolution image for presentation on an integrated display, and a higher resolution image for presentation on an external display; and
   send the raw ultrasound data without frame processing as acquired by the probe to an external device for at least one of storage or further processing.

20. The medium or media of claim 19, wherein the processor uses a stored instructions in accordance with user command received via the user interface, to perform one of:
   reconstruction using the raw ultrasound data without frame processing as acquired by the probe and display a resulting medical image at a first resolution on the integrated display; or
   reconstruction using the raw ultrasound data without frame processing as acquired by the probe and display the resulting medical image at the second, higher resolution on the external display or printer.

21. The medium or media of claim 19, wherein the processor uses a stored instructions in accordance with user command received via the user interface, to perform one of:
    reconstruction using the raw ultrasound data without frame processing as acquired by the probe; and
    transfer the raw ultrasound data to the external device for further processing or storage.

22. The medium or media of claim 19, wherein the processor uses an instruction to perform one of (i) sending the acquired raw ultrasound data to an external device across a wired or wireless medium and (ii) processing the acquired raw ultrasound data by a beam former and storing the processed raw ultrasound data in memory.

23. The medium or media of claim 19, wherein the instructions instruct the processor to label a soft key on the integrated display.

* * * * *